US012406753B2

United States Patent
Chang et al.

(10) Patent No.: US 12,406,753 B2
(45) Date of Patent: Sep. 2, 2025

(54) DIAGNOSTIC LABORATORY SYSTEMS AND METHODS OF IMAGING TUBE ASSEMBLIES

(71) Applicant: Siemens Healthcare Diagnostics Inc., Tarrytown, NY (US)

(72) Inventors: Yao-Jen Chang, Princeton, NJ (US); Vivek Singh, Princeton, NJ (US); Boris Mailhe, Plainsboro, NJ (US); Benjamin S. Pollack, Jersey City, NJ (US); Ankur Kapoor, Plainsboro, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 18/834,427

(22) PCT Filed: Mar. 2, 2023

(86) PCT No.: PCT/US2023/063622
§ 371 (c)(1),
(2) Date: Jul. 30, 2024

(87) PCT Pub. No.: WO2023/168366
PCT Pub. Date: Sep. 7, 2023

(65) Prior Publication Data
US 2025/0166748 A1  May 22, 2025

Related U.S. Application Data

(60) Provisional application No. 63/268,846, filed on Mar. 3, 2022.

(51) Int. Cl.
*G16H 10/40* (2018.01)

(52) U.S. Cl.
CPC .................. *G16H 10/40* (2018.01)

(58) Field of Classification Search
CPC ...................................... G16H 10/40
(Continued)

(56) References Cited

U.S. PATENT DOCUMENTS 9,704,054 B1 * 7/2017 Tappen .................. G06F 18/23
10,140,705 B2 11/2018 Wu et al.
(Continued)

FOREIGN PATENT DOCUMENTS

CN   114065874 A    2/2022
EP    1394727 B1   12/2011
(Continued)

OTHER PUBLICATIONS

Bochkovskiy, Alexey, et al. "Yolov4: Optimal speed and accuracy of object detection." arXiv preprint arXiv:2004.10934, 2020.
(Continued)

*Primary Examiner* — Michael Tomaszewski

(57) ABSTRACT

A method of synthesizing an image of a tube assembly includes capturing an image of the tube assembly, wherein the capturing generates a captured image. The captured image is decomposed into a plurality of features in latent space using a trained image decomposition model. One or more of the features in the latent space is manipulated into one or more manipulated features. A synthesized tube assembly image is generated with at least one of the manipulated features using a trained image composition model. Other methods and systems are disclosed.

20 Claims, 10 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 10,207,402 | B2 | 2/2019 | Levine et al. |
| 10,290,090 | B2 | 5/2019 | Chang et al. |
| 10,319,092 | B2 | 6/2019 | Wu et al. |
| 10,325,182 | B2 | 6/2019 | Soomro et al. |
| 10,668,622 | B2 * | 6/2020 | Pollack ............... B25J 11/0085 |
| 10,725,060 | B2 | 7/2020 | Chang et al. |
| 10,974,394 | B2 | 4/2021 | Benaim et al. |
| 2015/0278625 | A1 | 10/2015 | Finkbeiner et al. |
| 2017/0285122 | A1 | 10/2017 | Kaditz et al. |
| 2019/0294923 | A1 * | 9/2019 | Riley ..................... G06F 18/24 |
| 2020/0051017 | A1 | 2/2020 | Dujmic |
| 2021/0125065 | A1 | 4/2021 | Turcot et al. |
| 2021/0303818 | A1 | 9/2021 | Randolph et al. |
| 2021/0374519 | A1 | 12/2021 | Chen et al. |
| 2022/0076395 | A1 | 3/2022 | Amthor et al. |
| 2022/0114725 | A1 | 4/2022 | Amthor et al. |

FOREIGN PATENT DOCUMENTS

| | | | |
|---|---|---|---|
| JP | 2009223437 A | | 10/2009 |
| JP | 2021107810 A | | 7/2021 |
| WO | 2020027923 A1 | | 2/2020 |
| WO | 2020070876 A1 | | 4/2020 |
| WO | 2021086725 A1 | | 5/2021 |
| WO | 2021188596 A1 | | 9/2021 |
| WO | 2021225876 A1 | | 11/2021 |
| WO | 2022174240 A1 | | 8/2022 |
| WO | 2022174241 A1 | | 8/2022 |
| WO | 2022254600 A1 | | 12/2022 |
| WO | 2022266628 A1 | | 12/2022 |
| WO | 2023283583 A1 | | 1/2023 |
| WO | WO-2023168366 A2 * | 9/2023 | ............. G06V 10/82 |

OTHER PUBLICATIONS

Kupyn, Orest, et al. "Deblurgan-v2: Deblurring (orders-of-magnitude) faster and better." Proceedings of the IEEE/CVF international conference on computer vision. pp. 8878-8887. 2019.

Wojke, Nicolai, et al. "Simple online and realtime tracking with a deep association metric." 2017 IEEE international conference on image processing (ICIP). IEEE, 2017.

International Search Report and Written Opinion of International Application No. PCT/US2023/063622 dated Oct. 4, 2023.

Gat et al., "Latent Space Explanation by Intervention"; published: 2021; pp. 1-9; Retrieved from the Internet:<URL: https://arxiv.org/pdf/2112.04895.pdf>.

Tiu et al., "Understanding Latent Space in Machine Learning"; Towards Data Science; published: Feb. 4, 2020; pp. 2-6; Retrieved from the Internet:<https://towardsdatascience.com/understanding-latent-space-in-machine-learning-de5a7c687d8d>.

Liu et al., "Latent Space Cartography: Visual Analysis of Vector Space Embeddings"; pp. 1-12; Computer Graphics Forum: Eurographics Conference on Visualization (EuroVis) 2019; vol. 38; nr. 3; published: 2019.

Sengupta et al. "SfSNet: Learning Shape, Reflectance and Illuminance of Faces in the Wild," Proceedings of the IEEE Conference on Computer Vision and Pattern Recognition (CVPR), 2018, pp. 6296-6305.

Shoshan et al., "GAN-Control: Explicitly Controllable GANs," arXiv:2101.02477, v1, Jan. 2021.

Lee et al., "Diverse Image-to-Image Translation via Disentangled Representations," ECCV 2018.

Arash Vahdat, Jan Kautz, "NVAE: A Deep Hierarchical Variational Autoencoder" 34th Conference on Neural Information Processing Systems (NeurIPS 2020), pp. 1-21.

Razavi et al., "Generating diverse high-fidelity images with vq-vae-2." Advances in neural information processing systems 32 (2019).

Chen, Fu Shang et al.:; "Representation Decomposition for Image Manipulation and Beyond"; https://doi. org/10.48550/arXiv.2011.00788; Published at IEEE International Conference in Image Processing (ICIP) 2021; 19.09.2019; XP034123143.

Kazemi, Hadi et al.:; "Style and Content Disentanglement in Generative Adversarial Networks"; Computer Vision and Pattern Recognition (cs.CV); pp. 848-856; XP033525705; 07.01.2019.

Awiszus Maren et al..; "Learning Disentangled Representations via Independent Subspaces"; Accepted at ICCV 2019 Workshop on Robust Subspace Learning and Applications in Computer Vision; pp. 560-568; 27.10.2019; XP033732488.

Chen, T., Kornblith, S., Norouzi, M., & Hinton, G. (Oct. 26, 2020). A simple framework for contrastive learning of visual representations. In International conference on machine learning (pp. 1597-1607). PMLR.

Chen, T., Kornblith, S., Swersky, K., Norouzi, M., & Hinton, G. E. (Jul. 1, 2020). Big self-supervised models are strong semi-supervised learners. Advances in neural information processing systems, 33, 22243-22255.

Grill, J.B., Strub, F., Altche, F., Tallec, C., Richemond, P., Buchatskaya, E., Doersch, C., Avila Pires, B., Guo, Z., Gheshlaghi Azar, M. and Piot, B., (Sep. 10, 2020). Bootstrap your own latent-a new approach to self-supervised learning. Advances in neural information processing systems, 33, pp. 21271-21284.

He, K., Fan, H., Wu, Y., Xie, S., & Girshick, R. (Mar. 23, 2020). Momentum contrast for unsupervised visual representation learning. In Proceedings of the IEEE/CVF conference on computer vision and pattern recognition (pp. 9729-9738).

Tan, M., & Le, Q. (Jun. 23, 2021). EfficientNetV2: Smaller models and faster training. In International conference on machine learning (pp. 10096-10106). PMLR.

Zbontar, J., Jing, L., Misra, I., LeCun, Y., & Deny, S. (Jun. 14, 2021). Barlow twins: Self-supervised learning via redundancy reduction. In International conference on machine learning (pp. 12310-12320). PMLR.

Beck Michael A et al: "An embedded system for the automated generation of labeled plant images to enable machine learning applications, in agriculture", Arxiv.Org, Cornell University Library, 201 Olin Library Cornell University Ithaca, Ny 14853, Apr. 1, 2021 (Apr. 1, 2021), XP081923901, DOI: 10.1371/JOURNAL.PONE.0243923.

Marion Pat et al: "Label Fusion: A Pipeline for Generating Ground Truth Labels for Real RGBD Data of Cluttered Scenes", 2018 IEEE International Conference On Robotics and Automation (ICRA) , IEEE, May 21, 2018 (May 21, 2018), pp. 1-8, XP033403399, DOI: 10.1109/ICRA. 2018.8460950.

* cited by examiner

DIAGNOSTIC LABORATORY SYSTEMS AND METHODS OF IMAGING TUBE ASSEMBLIES

CROSS-REFERENCE TO RELATED APPLICATIONS

This application is a 35 U.S.C. 371 national application of international application no. PCT/US2023/063622 filed Mar. 2, 2023, which claims priority to U.S. Provisional application No. 63/268,846 filed Mar. 3, 2022, the contents of which are fully incorporated herein by reference.

FIELD

Embodiments of the present disclosure relate to diagnostic laboratory systems and methods of imaging tube assemblies in diagnostic laboratory systems.

BACKGROUND

Diagnostic laboratory systems conduct clinical chemistry or assays to identify analytes or other constituents in biological samples such as blood serum, blood plasma, urine, interstitial liquid, cerebrospinal liquids, and the like. The samples may be received in and/or transported throughout a system in sample tube assemblies.

Many of the laboratory systems process large volumes of tube assemblies and the samples in the tube assemblies. Some laboratory systems make use of machine vision and machine learning to facilitate sample processing and tube assembly identification (e.g., characterization). For example, vision-based machine learning models (e.g., AI models) have been adopted to provide fast and noninvasive methods for tube assembly identification and fluid characterization. However, the training cost for adding new tube assemblies may be excessive because large amounts of training data may be required to retrain or adapt the machine learning models to characterize the new tube assemblies.

Tube assembly manufacturers continuously produce new tube assembly configurations to either bring in new features or save production costs. In addition, third-party low-cost tube assembly replacements may be utilized by some laboratories due to availability and/or financial reasons. With so many tube assembly configurations, it is difficult to collect every possible tube assembly variation across the globe, which means that the machine learning models likely cannot be trained on all the tube assembly configurations. Accordingly, there is a limit to the number of tube assembly configurations the machine learning models can handle in practice. Therefore, a need exists for laboratory systems and methods that facilitate the introduction of new tube assembly configurations into the laboratory systems.

SUMMARY

According to a first aspect, a method of synthesizing an image of a tube assembly is provided. The method includes capturing an image of a tube assembly, the capturing generating a captured image; decomposing the captured image into a plurality of features in latent space using a trained image decomposition model; manipulating one or more of the features in the latent space into manipulated features; and generating a synthesized tube assembly image with at least one of the manipulated features using a trained image composition model.

In a further aspect, a method of synthesizing images of tube assemblies is provided. The method includes constructing an image decomposition model configured to receive input images of tube assemblies and to decompose the input images to a plurality of features in a latent space; constructing an image composition model configured to compose synthetic tube assembly images based on the plurality of features in the latent space; and training the image decomposition model and the image composition model using at least an image of a first tube assembly and an image of a second tube assembly with one or more known variations between the image of the first tube assembly and the image of the second tube assembly, wherein the training produces a trained image decomposition model and a trained image composition model.

In another aspect, a diagnostic laboratory system is provided. The diagnostic laboratory system includes an image decomposition model configured to receive input images of tube assemblies and to decompose the input images into a plurality of features in a latent space; and an image composition model configured to compose synthetic tube assembly images based on the plurality of features in the latent space, wherein the image decomposition model and the image composition model are trained using at least an image of a first tube assembly and an image of a second tube assembly with one or more known variations between the image of the first tube assembly and the second tube assembly.

Still other aspects, features, and advantages of this disclosure may be readily apparent from the following description and illustration of a number of example embodiments, including the best mode contemplated for carrying out the disclosure. This disclosure may also be capable of other and different embodiments, and its several details may be modified in various respects, all without departing from the scope of the disclosure. This disclosure is intended to cover all modifications, equivalents, and alternatives falling within the scope of the claims and their equivalents.

BRIEF DESCRIPTION OF THE DRAWINGS

The drawings, described below, are provided for illustrative purposes, and are not necessarily drawn to scale. Accordingly, the drawings and descriptions are to be regarded as illustrative in nature, and not as restrictive. The drawings are not intended to limit the scope of the disclosure in any way.

DETAILED DESCRIPTION

Figure 1:
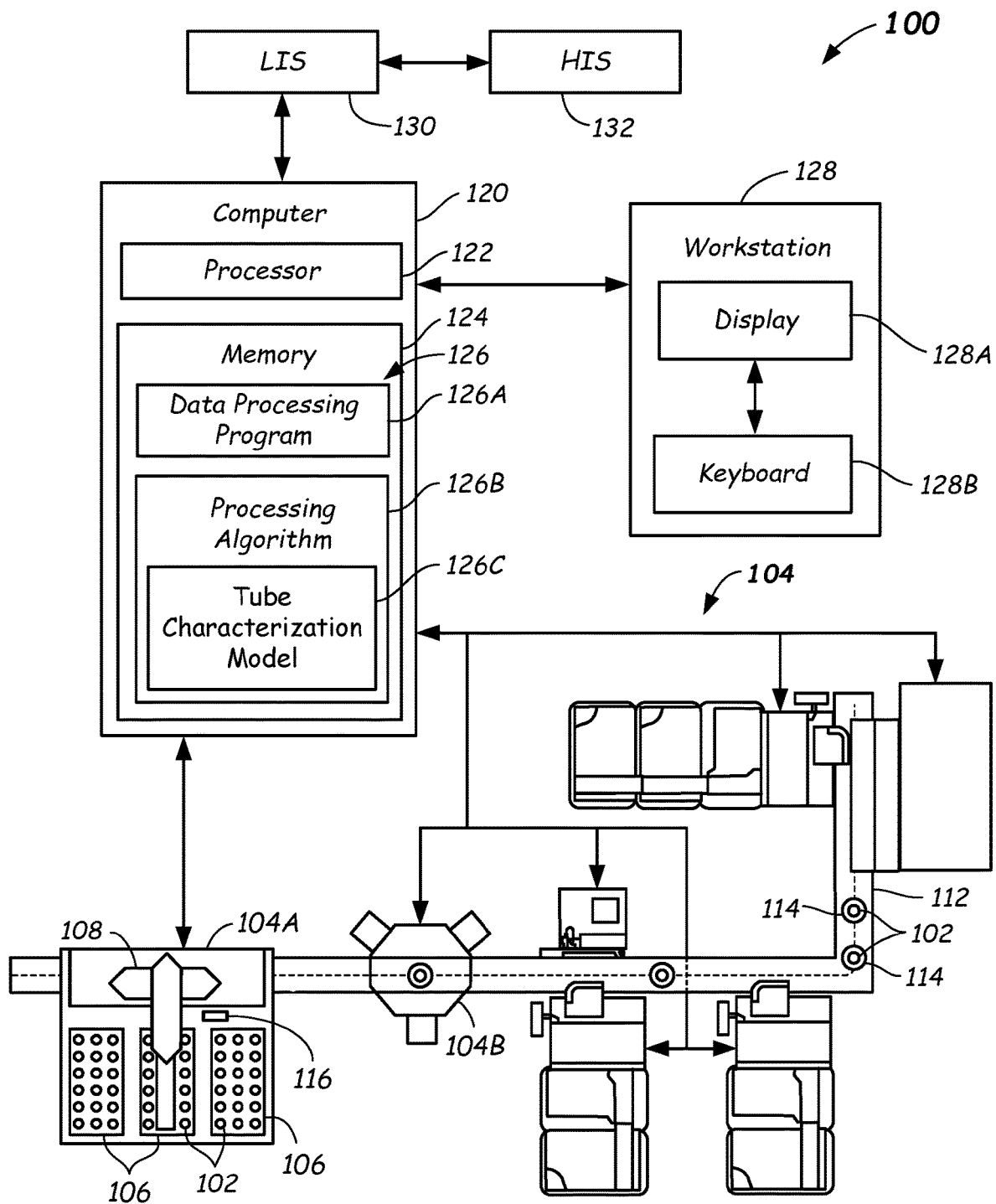
FIG. 1 illustrates a block diagram of a diagnostic laboratory system including a plurality of instruments according to one or more embodiments.

Diagnostic laboratory systems conduct clinical chemistry and/or assays to identify analytes or other constituents in biological samples such as blood serum, blood plasma, urine, interstitial liquid, cerebrospinal liquids, and the like. The samples are collected in tube assemblies (e.g., sample tubes) and transported via the tube assemblies to the laboratory systems where the samples are analyzed. In some embodiments, the tube assemblies are transported throughout the laboratory system so that various instruments may perform the analyses.

Laboratory systems may use tube assemblies from various manufacturers to collect samples and transport the samples to and throughout a laboratory system. A tube assembly may include a sample tube, such as a closed-bottomed tube. Some tube assemblies may include a cap that seals the tube. A tube assembly may also include the contents of the tube. Different tube assembly types may have different characteristics, such as different sizes and different chemical additives therein. For example, many tube assembly types are chemically active, meaning the tube assemblies contain one or more additive chemicals that are used to change or retain a state of the samples or otherwise assist in sample processing. In some embodiments, the inside wall of a tube may be coated with the one or more additives, or the additives may be provided elsewhere in the tubes. The types of additives contained in the tubes may be serum separators, coagulants such as thrombin, anticoagulants such as EDTA or sodium citrate, anti-glycosis additives, or other additives for changing or retaining a characteristic of the samples. The tube assembly manufacturers may associate the colors of the caps on the tubes and/or shapes of the tubes or caps with specific types of chemical additives contained in the tubes.

Different manufacturers may have their own standards for associating attributes of the tube assemblies, such as cap color, cap shape, and tube shape with particular properties of the tube assemblies. For example, the attributes may be related to the contents of the tubes or possibly whether the tubes are provided with vacuum capability. In some embodiments, a manufacturer may associate all tube assemblies with gray colored caps with tubes including potassium oxalate and sodium fluoride configured to test glucose and lactate. Tube assemblies with green colored caps may include heparin for stat electrolytes such as sodium, potassium, chloride, and bicarbonate. Tube assemblies with lavender caps may identify tubes containing EDTA (ethylenediaminetetraacetic acid-an anticoagulant) configured to test CBC w/diff., HgBA1c, and parathyroid hormone. Other cap colors such as red, yellow, light blue, royal blue, pink, orange, and black may be used to signify other additives or lack of an additive. In other embodiments, combinations of colors of the caps may be used, such as yellow and lavender to indicate a combination of EDTA and a gel separator, or green and yellow to indicate lithium heparin and a gel separator.

The laboratory systems may use the tube assembly attributes for further processing of the tubes and/or the samples. Since the tubes may be chemically active, it is important to associate specific tests that can be performed on samples with specific tube assembly types because the tests may be dependent on the contents of the tubes. Thus, the laboratories may confirm that tests being run on samples in the tubes are correct by analyzing the colors and/or shapes of the caps and/or the tubes. Other attributes may also be analyzed.

Transport mechanisms, such as robots and tube assembly carriers within the laboratory systems may have specific hardware and processes for moving different types of tube assemblies. For example, a robot may grasp a first type of tube assembly differently than a second type of tube assembly. In addition, the laboratory systems may utilize different carriers depending on the types of tube assemblies that are to be transported throughout the laboratory systems. Thus, the laboratory systems need to identify the tube assemblies.

The laboratory systems described herein may use vision systems to capture images of tube assemblies and identify the tube assemblies and/or contents of the tube assemblies. For example, the laboratory systems may include vision-based artificial intelligence (AI) models configured to provide fast and noninvasive methods for tube assembly characterization. Embodiments of the AI models may be trained to characterize different types of tube assemblies and slight variations of the tubes and/or the caps. As new types of tube assemblies are introduced into the laboratory systems, the AI models need to be updated to be able to classify the new types of tube assemblies. Retraining the AI models in conventional laboratory systems may be costly and time consuming because a plurality of tube assembly types need to be imaged and manually classified to retrain the AI models.

The systems and methods described herein overcome the problems with tube assembly classification by synthesizing images of tube assemblies. Images of synthetic data and/or paired tube assemblies may be used with controlled variations in the images to train an image decomposition model and an image composition model. The trained decomposition model is used to decompose images of tube assemblies into features (e.g., decomposed features) in latent space. One or more of the features in the latent space may then be manipulated. The trained composition model may reassemble the features, including a manipulated feature, to generate synthesized tube assembly images.

In some embodiments, image-to-image translation is used by the decomposition model and the composition model to synthesize images of the tube assemblies, wherein the new or synthesized images are controlled modifications of reference images. Image-to-image translation is a class of vision and graphics processing wherein the goal is to learn the mapping between an input image of a tube assembly and an output image of a tube assembly using a training set of aligned image pairs. In some embodiments, the processing may include using a generative adversarial network (GAN) to perform the image-to-image translation. These and other systems and methods are described below in greater detail with reference to FIGS. 1-11.

Reference is now made to FIG. 1, which illustrates an example embodiment of an automated diagnostic system 100 configured to process and/or analyze biological samples stored in tube assemblies 102 (e.g., sample containers). The tube assemblies 102 may be any suitable containers (e.g., tubes), including transparent or translucent containers, such as blood collection tubes, test tubes, sample cups, cuvettes, or other containers capable of containing samples and/or allowing imaging of the samples contained therein. The tube assemblies may or may not have caps or lids attached thereto. As described herein, the tube assemblies 102 may have different sizes and may have different cap colors and/or cap types. As described herein, the system 100 and methods described herein enable the system 100 or devices coupled to the system 100 to generate images that synthesize different tube assemblies.

The system 100 may include a plurality of instruments 104 that are configured to process the tube assemblies 102 and/or samples located in the tube assemblies 102. The tube assemblies 102 may be received at the system 100 at an input/output instrument 104A that may include on one or more racks 106 and a robot 108. The robot 108 may transport the tube assemblies 102 between the racks 106 and carriers 114 located on a track 112. The carriers 114 are configured to transport the tube assemblies 102 on the track 112.

The instruments 104 may process the samples and/or the tube assemblies 102. The processing may include preprocessing or prescreening the samples and/or the tube assemblies 102 prior to analysis by one or more of the instruments 104. For example, the preprocessing may prepare samples for specific assays or other analyses. Preprocessing may also identify the types of tube assemblies 102 to prepare the samples for analyses in response to the identification. Other ones of the instruments 104 may perform the analyses on the samples.

One or more of the instruments 104 may include an imaging device that captures images of the tube assemblies 102 and/or the carriers 114. In the embodiment of FIG. 1, an imaging instrument 104B may include imaging devices as described below and may be configured to capture images of the tube assemblies 102 and/or the carriers 114. In some embodiments, an imaging device 116 may be located in or proximate the input/output instrument 104A and may be configured to capture images of the tube assemblies 102 prior to the tube assemblies 102 being transferred to the track 112 or loaded into the carriers 114.

Figure 2:
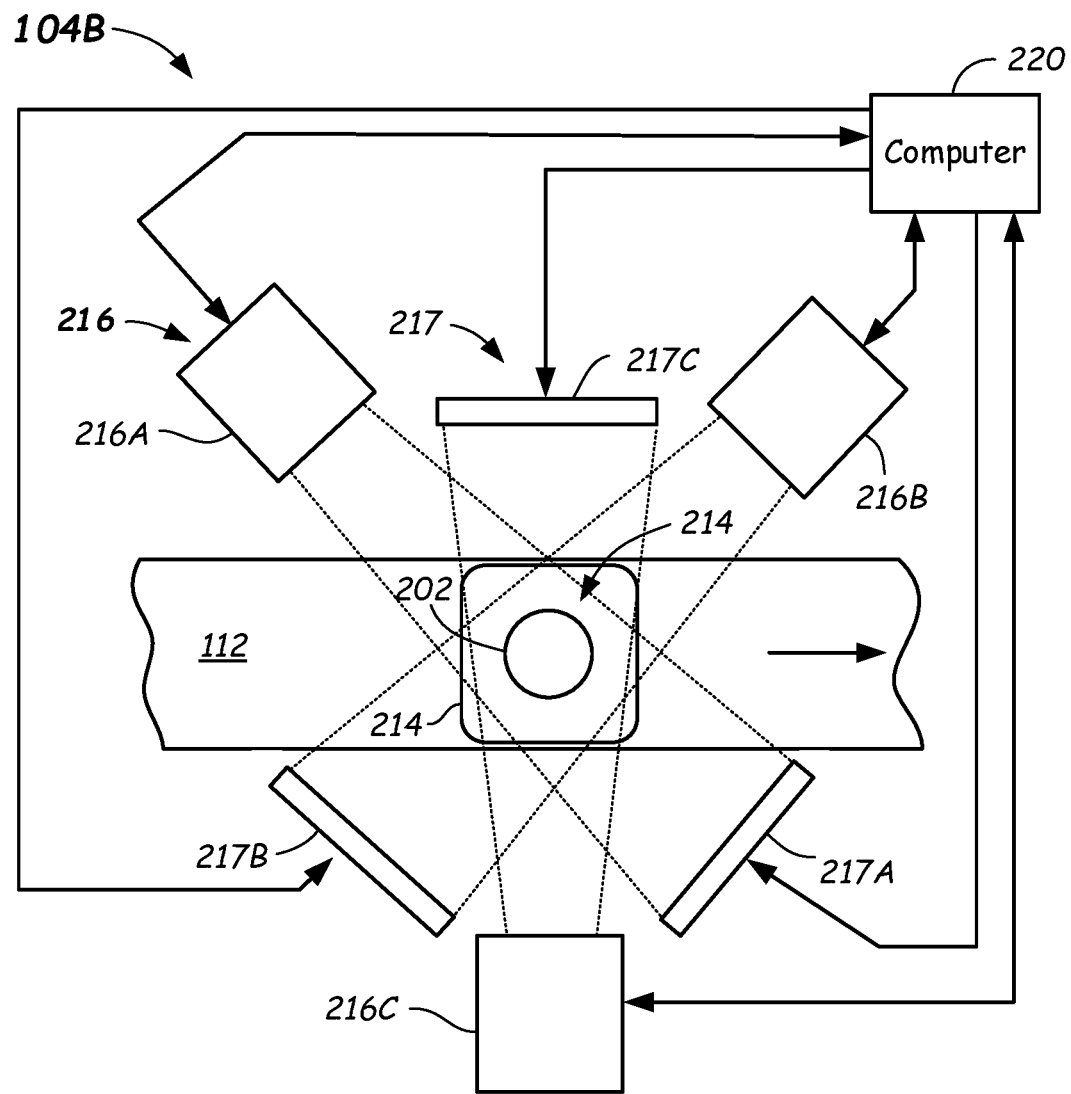
FIG. 2 illustrates a top plan view of an imaging instrument provided in a diagnostic laboratory system according to one or more embodiments.

Additional reference is made to FIG. 2, which illustrates a top plan view of the imaging instrument 104B. Other embodiments of imaging instruments may be implemented in the system 100. In the embodiment of FIG. 2, the imaging instrument 104B is configured to capture images of the tube assemblies 102 while the tube assemblies 102 are located on the track 112. A tube assembly 202 is shown located on the track 112 and at an imaging location 214 within the imaging instrument 104B. The components of the imaging instrument 104B may be controlled by a computer 220. In some embodiments, the computer 220 may be incorporated into the computer 120 (FIG. 1).

The imaging instrument 104B may include three imaging devices 216 configured to capture images of the tube assembly 202 at the imaging location 214. The imaging devices 216 are referred to individually as a first imaging device 216A, a second imaging device 216B, and a third imaging device 216C. In other embodiments, the imaging instrument 104B may include one or more imaging devices. The imaging devices 216 may be configured to generate image data representative of the tube assembly 202. The computer 220 and/or the computer 120 (FIG. 1) may be configured to process the image data generated by the imaging devices 216 as described herein.

The imaging instrument 104B may also include one or more illumination devices 217 that are configured to illuminate the imaging location 214. Thus, the illumination devices 217 may be configured to illuminate the tube assembly 202. In the embodiment of FIG. 2, the imaging instrument 104B may include three illumination devices 217, which are referred to individually as a first illumination device 217A, a second illumination device 217B, and a third illumination device 217C.

Referring again to FIG. 1, the system 100 may also include or be coupled to a computer 120 that may be configured to operate and/or communicate with the instruments 104. In some embodiments, the computer 120 may analyze data received in the system 100 and/or generated by the instruments 104. The computer 120 and programs executed by the computer 120 may also analyze image data generated by the imaging instrument 104B and other imaging devices as described herein. The computer 120 may include a processor 122 configured to execute computer-readable instructions (e.g., program code).

In the embodiment of FIG. 1, the computer 120 may be connected to individual ones of the instruments 104. For example, the computer 120 may be connected to the computer 220 in the imaging instrument 104B. In some embodiments, the computer 120 may be coupled to one or more workstations (not shown) coupled to one or more of the instruments 104. In some embodiments, the computer 120 may be configured to transmit computer instructions and/or computer code to individual ones of the instruments 104. In some embodiments, the computer 120 may be configured to receive and/or process data generated by the instruments 104.

The computer 120 may include or be coupled to memory 124 that may store or access one or more modules and/or programs 126, which are described herein as being stored in the memory 124. The modules or programs 126 may be executable by the processor 122. The programs 126 may be configured to operate one or more of the instruments 104. Although the programs are described as individual programs, in some embodiments the programs 126 may be implemented as a single program. One or more of the programs 126 may execute artificial intelligence (AI) algorithms. The programs 126 may include a data processing program 126A that may be configured to process data in at least one of the instruments 104, including the imaging instrument 104B. For example, the data processing program 126A may process data input to the system 100 and/or one or more of the instruments 104. The data processing program 126A may also process data generated by one or more of the instruments 104.

In some embodiments, the memory 124 may include a processing algorithm 126B. In some embodiments, the memory 124 may include two or more processing algorithms. In some embodiments, the two or more processing algorithms may be implemented as a single processing algorithm, such as the processing algorithm 126B. The processing algorithm 126B may include computer code configured to analyze image data and other data generated by imaging devices in the system 100 or coupled to the system 100. In some embodiments, the processing algorithm 126B may process data using AI, which may be implemented as a tube characterization model 126C that analyzes image data as described herein. The tube characterization model 126C may be updated as described herein. For example, an image decomposition model 502 (FIG. 5) and/or an image composition model 504 (FIG. 5) may be updated as described herein.

The imaging devices 216 and computers (e.g., computer 120) used to process images captured by the imaging devices 216 may be part of machine vision and machine learning used by the system 100 to facilitate processing of the tube assemblies 102. For example, as described herein, the machine vision and AI models that may be running in the tube characterization model 126C may identify specific types of tube assemblies 102 and/or samples located in the tube assemblies 102 to facilitate sample processing and analyses as described herein.

The computer 120 may be coupled to or implemented in a workstation 128. The workstation 128 may enable user interaction with the system 100 and/or one or more of the instruments 104. The workstation 128 may include a display 128A and/or a keyboard 128B that enable users to interface with the system 100 and/or individual ones of the instruments 104.

In some embodiments, the system 100 may be coupled to a laboratory information system (LIS) 130 that may determine how samples are to be tested by the system 100. In some embodiments, the LIS 130 may be implemented in the computer 120. The LIS 130 may be coupled to a hospital information system (HIS) 132 that may receive specific assay orders for specific samples. The HIS 132 may also receive assay results after assays are performed on the specific samples by the system 100.

In an example of the operation of the system 100, a doctor may order a specific test to be performed on a sample from a patient. The doctor may enter the test order into the HIS 132. The HIS 132 may then transmit the test order to the LIS 130. The sample may be drawn from the patient and placed into a tube assembly, such as the tube assembly 202 (FIG. 2). The configuration of the tube assembly 202, such as color, size, and shape, may correspond to the type of test in the test order. The tube assembly 202 may then be delivered to the system 100. The LIS 130 may determine how the sample is to be tested and may transmit this information to the computer 120 where instructions may be generated to operate the instruments 104 to perform the test. For example, the data processing program 126A may generate the instructions. The imaging devices 216 (FIG. 2) may generate images of the tube assembly 202 and, based on the image data, the tube characterization model 126C may identify the type of the tube assembly 202. The testing and movement of the tube assembly 202 throughout the system 100 may be at least partially based on the type of tube assembly 202. After testing is complete, the LIS 130 may transmit the test results to the HIS 132.

Figures 3A, 3B, 3C:
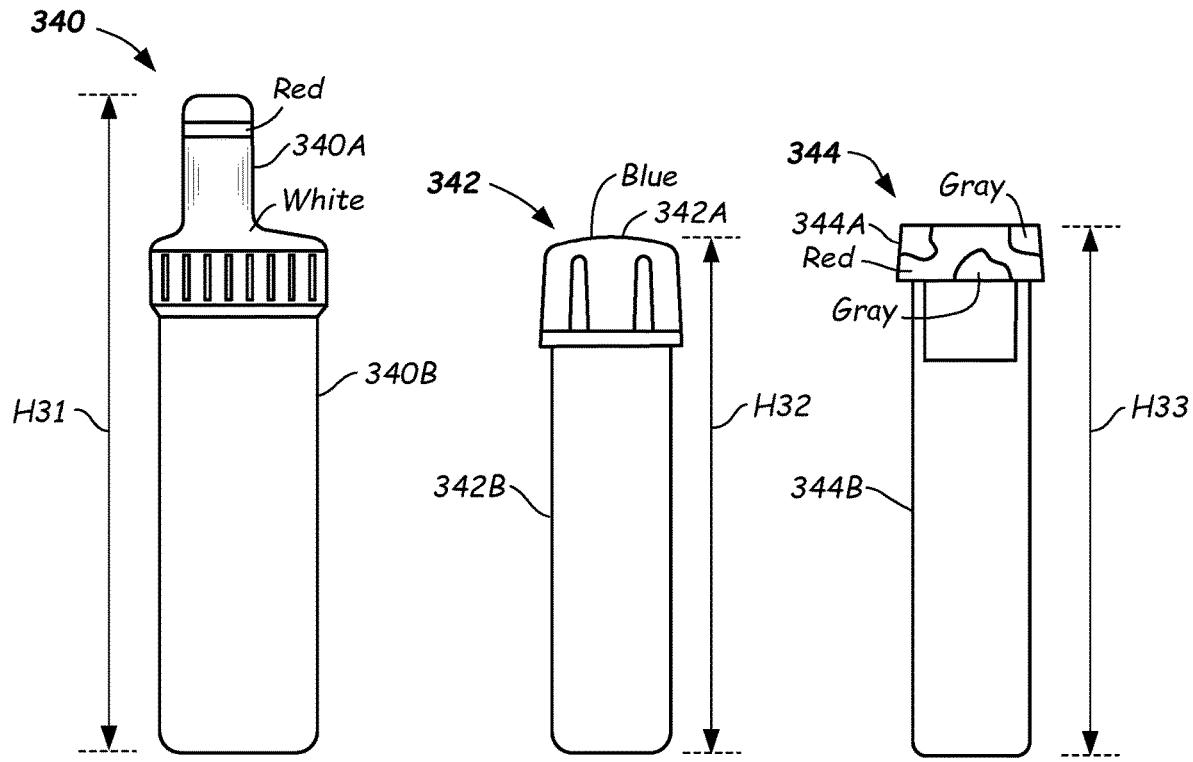
FIGS. 3A-3C illustrate different types of tube assemblies including caps affixed to tubes that may be used within a diagnostic laboratory system according to one or more embodiments.

Additional reference is now made to FIGS. 3A-3C, which illustrate different types of tube assemblies that may be used within the system 100. Tube assemblies refer to tubes with or without caps attached to the tubes. Tube assemblies may also include samples or other contents of the tube assemblies. Additional reference is also made to FIGS. 4A-4C, which illustrate the tube assemblies of FIGS. 3A-3C without the caps. As shown in the figures, all the tube assemblies have different configurations or geometries. The caps may each have a different cap geometry.

Figures 4A, 4B, 4C:
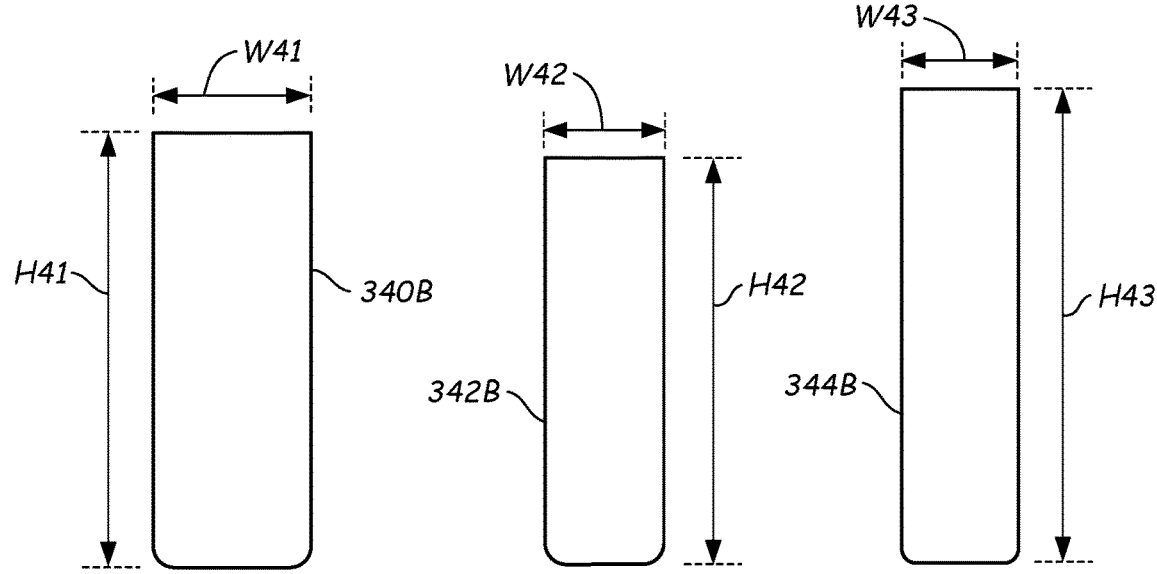
FIGS. 4A-4C illustrate different types of tubes of tube assemblies that may be used within a diagnostic laboratory system according to one or more embodiments.

A tube assembly 340 of FIG. 3A includes a cap 340A that is white with a red stripe and has an extended vertical portion. The cap 340A may fit over a tube 340B. The tube assembly 340 has a height H31. FIG. 4A illustrates the tube 340B without the cap 340A. The tube 340B has a height H41 and a width W41.

A tube assembly 342 of FIG. 3B includes a cap 342A that is blue with a dome-shaped top. The cap 342A may fit over a tube 342B. The tube assembly 342 has a height H32. FIG. 4B illustrates the tube 342B without the cap 342A. The tube 342B has a height H42 and a width W42.

A tube assembly 344 of FIG. 3C includes a cap 344A that is red and gray with a flat top. The cap 344A may fit over a tube 344B. The tube assembly 344 has a height H33. FIG. 4C illustrates the tube 344B without the cap 344A. The tube 344B has a height H43 and a width W43.

FIGS. 3A-4C illustrate different types of tubes, caps, and tube assemblies that may be used in the system 100. The tube characterization model 126C may have been trained to characterize or identify the tubes, caps, and tube assemblies of FIGS. 3A-4C. In some embodiments, the tube characterization model 126C may also determine whether the tube assemblies are not able to be characterized. In some embodiments, the tubes may have shapes other than the cylindrical shapes of FIGS. 3A-4C and may be characterized by the tube characterization model 126C. In addition, the tubes and caps may be made of different materials and may have different shapes, structures, albedo, and textures that may be characterized by the tube characterization model 126C.

Over time, laboratories may utilize tube assemblies from sources that provide tube assemblies that deviate from tube assemblies supplied by manufacturers on which the tube characterization model 126C was trained. For example, the laboratories may use tube assemblies supplied by local manufacturers or new tube assembly designs that are not stored in the tube characterization model 126C. The training data may be limited and may limit the number of tube variations the tube characterization model 126C may identify or characterize. Retraining the tube characterization model 126C to handle different tube types typically requires training with large numbers of images illustrating different configurations of tube assemblies under different views and lighting conditions. In some conventional embodiments, the training is performed manually, which makes the retraining costs very high.

The embodiments disclosed herein synthesize tube assembly images to generate synthetic tube assembly images. In one example, the tube characterization model 126C is trained to characterize specific types of tube assemblies that may be used for specific tests. The tube assemblies may have specific tube materials, tube colors, tube shapes, cap shapes, cap colors, and other unique attributes. Over time, one or more manufacturers may change these attributes of the tube assemblies. The embodiments disclosed herein enable the system 100, such as the processing algorithm 126B, to synthesize images of tube assemblies with the new attributes, which may then be used to by the tube characterization model 126C to characterize the new tube assemblies.

In another example, the system 100 may receive a new tube assembly type from a new manufacturer. Each attribute of the new tube assembly type may be similar to the attributes of a specific tube assembly on which the tube characterization model 126C has been trained. For example, the new tube assembly may have the same tube material as a tube assembly on which the tube characterization model 126C has been trained but with a different cap shape. While another tube assembly type on which the tube characterization model 126C was trained may have the same cap type as a new tube assembly type, but with a different tube material.

The system 100, using the tube characterization model 126C, may synthesize images of the new tube assembly with the different cap shape. In some embodiments, the system 100 may synthesize the image using a similar cap shape from another type or tube assembly. In other embodiments, the system 100 may synthesize the cap shape of the new tube assembly.

Some embodiments disclosed herein may use unpaired or paired image-to-image translation to adapt existing data (e.g., image data) from existing tube assembly types to new tube assembly types. The existing data may be the images used to train the tube characterization model 126C. The image-to-image translation may be performed using machine learning, such as deep learning (DL) methods. An example of the machine learning includes generative adversarial networks (GANs). An example of a GAN is cycle-GAN which performs unpaired image-to-image translation using cycle-consistent adversarial networks. Some embodiments decompose a captured image of a tube assembly into decomposed features. One or more of the decomposed features may be translated into a synthesized tube assembly image or into a portion of a synthesized tube assembly. Thus, the systems and methods disclosed herein enable collection of data (e.g., images) from existing tube assembly configurations to develop synthesized images of different tube assemblies.

Figure 5:
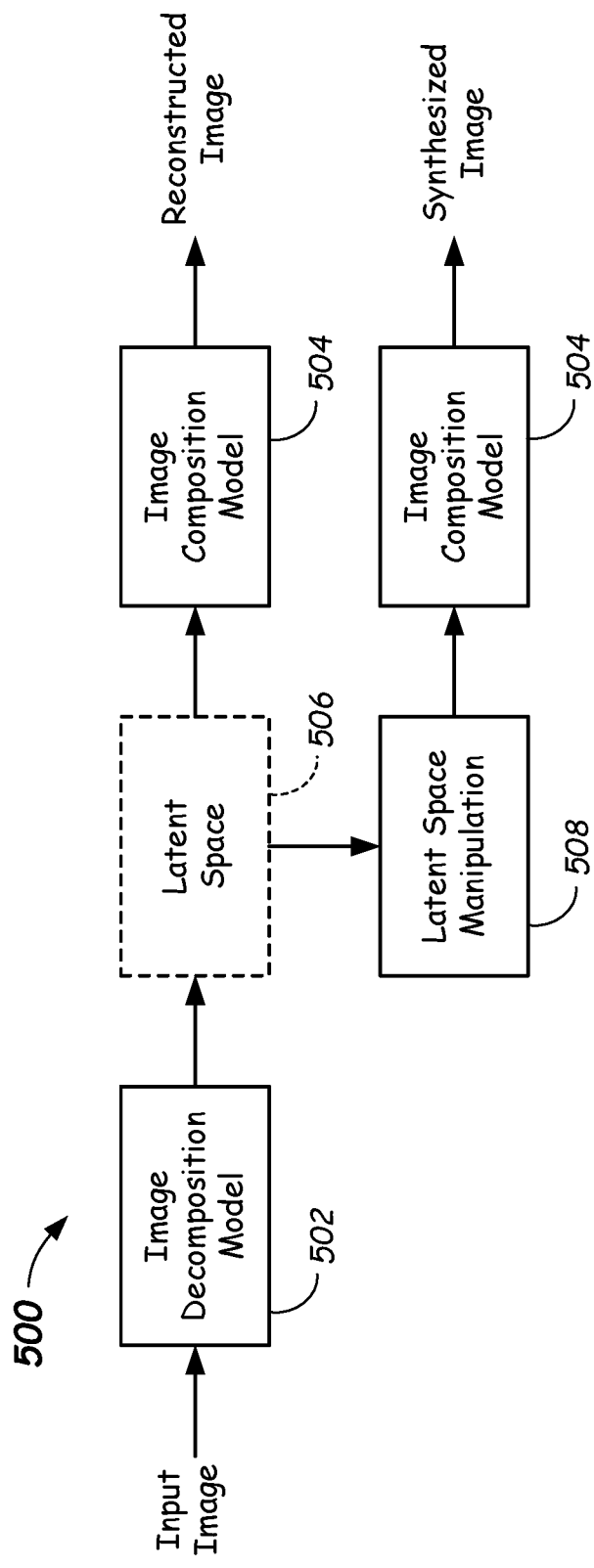
FIG. 5 illustrates a block diagram of a process that implements a method of synthesizing images of tube assemblies according to one or more embodiments.

Additional reference is made to FIG. 5, which illustrates a block diagram of a process 500 that implements a method of synthesizing images of tube assemblies as described herein. The images referred to in FIG. 5 may be image data, such as image data generated by the imaging instrument 104B. The process 500 uses synthesized data or images of paired tube assemblies with controlled variations to train an image decomposition model 502 and an image composition model 504. The trained image decomposition model 502 may then receive input images of tube assemblies and decompose the input images into latent space 506 having a plurality of features. A latent space manipulation module 508 may manipulate one or more features of the images in the latent space 506. For example, the latent space manipulation module 508 may manipulate one or more features in the latent space that are related to an attribute such as the cap color of an image of a tube assembly. The manipulated features may then be used by the image composition model 504 to generate synthesized images of the tube assemblies.

Figure 6:
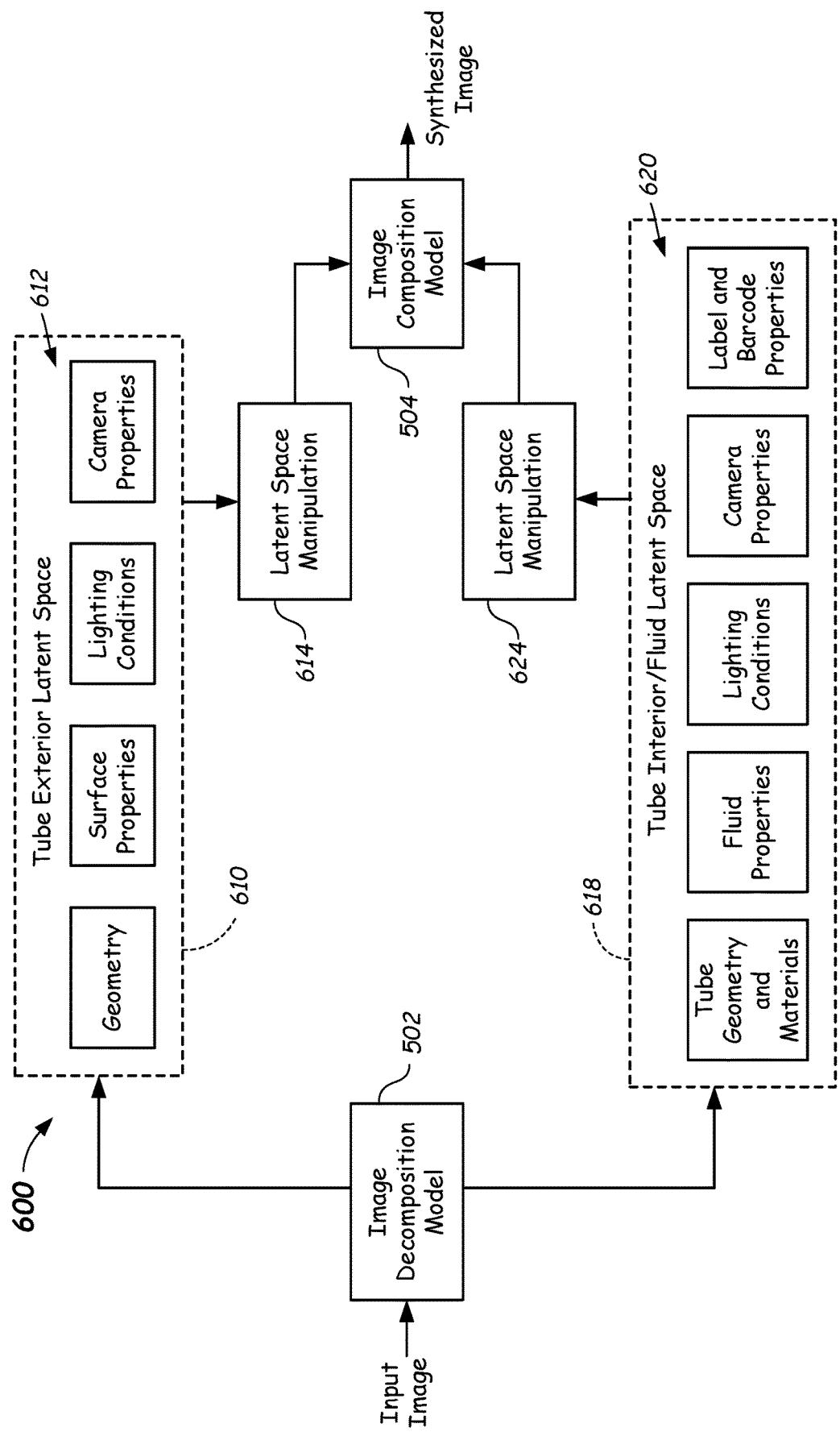
FIG. 6 illustrates a block diagram of a process that implements a method of synthesizing images of exteriors and interiors of tube assemblies according to one or more embodiments.

FIG. 6 illustrates a block diagram of a process 600 that implements a method of synthesizing images of tube assembly exterior surfaces and tube assembly interiors according to one or more embodiments. The tube assembly interior synthesis may synthesize fluids in the tube assemblies. In some embodiments, the process 600 may be considered two separate processes.

The process 600 may include decomposing images using the image decomposition model 502 described in FIG. 5 that decomposes input images into various features. The process 600 may use a tube exterior latent space 610 configured to characterize exterior attributes of images of the tube assemblies. The tube exterior latent space 610 may include individual variables or features 612 that may be configured to isolate different attributes of images of the tube assembly exteriors decomposed by the image decomposition model 502. The features 612 may isolate the images based on attributes such as geometries and materials of the tube assemblies, surface properties of the tube assemblies, lighting conditions under which the images are captured, and camera properties of imaging devices (e.g., imaging devices 216 of FIG. 2). Other attributes of the images may be isolated or characterized.

The tube exterior latent space 610 may be manipulated by a latent space manipulation module 614. The latent space manipulation module 614 may be identical or substantially similar to the latent space manipulation module 508 of FIG. 5. The latent space manipulation module 614 may manipulate features 612 isolated in the tube exterior latent space 610. The image composition model 504 may then compose the image using the manipulated features manipulated by the latent space manipulation module 614.

The process 600 may include decomposing images of tube interiors or fluids using the image decomposition model 502 described in FIG. 5. The process 600 may use a tube interior latent space 618 configured to synthesize interior attributes of images of the tube assemblies. In some embodiments, the tube interior latent space 618 may characterize contents of the tube assemblies, such as samples stored in the tube assemblies, into features 620. The tube interior latent space 618 may include individual variables or features 620 that may include geometries and materials of the tube assemblies, fluid properties, lighting conditions under which the images are captured, camera properties of imaging devices (e.g., imaging devices 216 of FIG. 2), and label and/or barcode properties. Other attributes of the images may be isolated or characterized into the features 620.

The features 620 of the tube interior latent space 618 may be manipulated by a latent space manipulation module 624. The latent space manipulation module 624 may be identical or substantially similar to the latent space manipulation module 614 or the latent space manipulation module 508 of FIG. 5. The latent space manipulation module 624 may manipulate features 620 isolated in the tube interior latent space 618. The image composition model 504 may then compose synthesized images of tube assemblies using the manipulated features.

Figure 7:
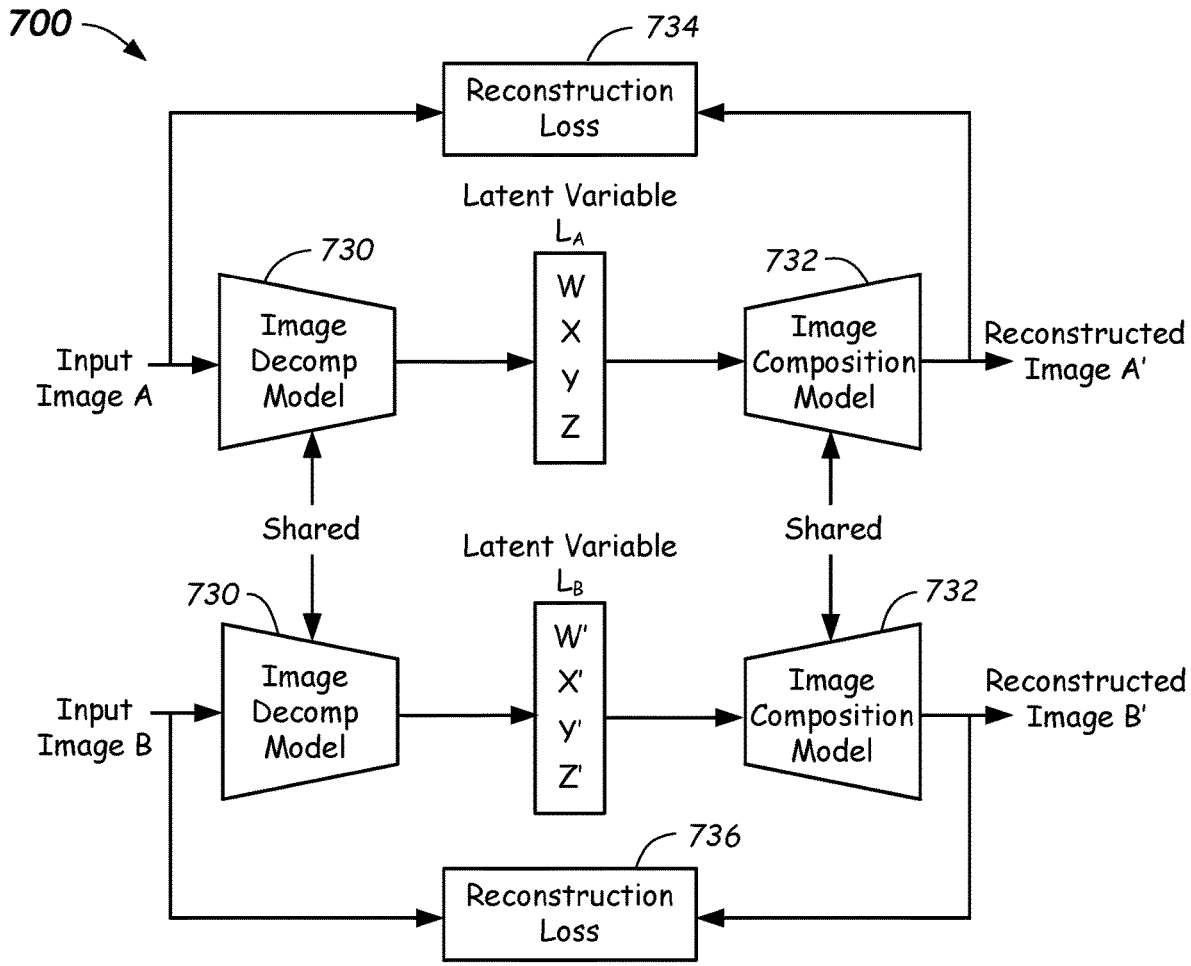
FIG. 7 illustrates a process that may be used to train an image decomposition model and an image composition model according to one or more embodiments.

Additional reference is made to FIG. 7, which is an embodiment of a training process 700 that may be used to train the image decomposition model 502 and the image composition model 504. A first image A of a first tube assembly is input to an encoder network that is implemented as a decomposition model 730 (sometimes referred to as an image decomposition model) that generates latent features in a latent variable LA in a multidimensional latent space. The decomposition model 730 may be similar or identical to the decomposition model 530. In some embodiments, the decomposition model 730 generates latent features in low-dimensional space. The features of the latent variable LA may be partitioned into multiple groups of features such as W, X, Y, and Z as shown in FIG. 7. Each of the features may correspond to a specific one of the attributes of a tube assembly. In some embodiments, at least one of the features (e.g., feature Z) may be reserved for an intrinsic property of images of the tube assemblies in which variations cannot be controlled by a setup. In some examples, all tubes in a study may have a cylindrical structure that all share in common such that it is expected that they all share the same values in feature Z.

A composition model 732 (sometimes referred to as an image composition model) that may be implemented as a decoder network may use the features of the latent variable LA to reconstruct an image A' of a tube assembly to be as similar to the input image A as possible. The composition model 732 may be similar or identical to the composition model 532. A reconstruction loss module 734 may compare the input image A to the output image A' to determine whether the images are close to each other. For example, the reconstruction loss module 734 may analyze the attributes of the image A and the image A' to determine whether the latent variable LA is correct and whether the decomposition model 730 and the composition model 732 are trained correctly.

The training process 700 may also include receiving a second input image B of a second tube assembly into the decomposition model 730 and generating latent features in a latent variable LB in multidimensional space. The images A and B may be paired tube assembly images. The features of the latent variable LB may be partitioned into multiple groups of features such as W', X', Y', and Z' as shown in FIG. 7. Each of the features may correspond to a specific one of the attributes of the tube assemblies. At least one of the features (e.g., feature Z') may be reserved for the intrinsic property of the tube image that cannot be captured by one of the features. The composition model 732 may use the features to reconstruct an image B' of a tube assembly to be as similar to the input image B as possible. A reconstruction loss module 736 may compare the input image B to the output image B' to determine whether the images are close to each other. For example, the reconstruction loss module 736 may analyze the attributes of the image B and the image B' to determine whether the latent variable LB is correct and whether the decomposition model 730 and the composition model 732 are trained correctly.

Training a disentangled latent space, such as used with the decomposition model 730 and the composition model 732, may include having the input image B be a specific variation relative to the input image A. For example, in the case of tube cap synthesis, a first feature (e.g., W and W) of the latent variable LA and the latent variable LB may be the albedo such as the color of tube caps. In this example, the input image B is the same tube assembly type as the input image A with the only variation being color of the tube cap. The input image B may either be generated synthetically such as generated using computer-generated imagery (CGI) or captured from the same type of tube assembly and the same imaging setup used to acquire the input image A. The tube cap in the input image B may be very similar to the cap in the input image A, with the only or only significant difference being a difference in cap colors. In the latent spaces LA and LB, the remaining features (e.g., X and X', Y and Y', Z and Z') are to be as similar as possible while allowing the first feature W and W to vary as described above.

The above process may be repeated for other variations in the latent spaces LA and LB, so that each of the features of the latent variables captures a particular variation. In some embodiments, it is possible to have multiple variations at the same time between input image A and input image B. In such embodiments, corresponding latent features may be allowed to vary while the remaining features are held consistent. As an example, input image A and input image B may be captured with the same camera, but include tube assemblies having different tube geometries, surface properties, and under different lighting conditions. In this embodiment, only the latent feature corresponding to camera properties are forced to be similar and the other features may vary.

The architecture of the training process 700 includes the decomposition model 730 and the composition model 732. Therefore, the training may be enhanced with unpaired images by training on those images to minimize the reconstruction loss only. Such images can also be edited in a latent domain by replacing some of their latent features with latent features taken from another image. Then the decomposition model 730 and the composition model 732 can be trained by an adversarial network trying to classify the edited and unedited images. For example, there may be a set of tube assembly images $S_1$ captured by a first imaging device $C_1$ (e.g., the first imaging device 216A of FIG. 2) with lighting condition $L_1$ provided by the first illumination device 217A. Latent features of images $S_1$ corresponding to camera properties of the first imaging device 216A and light conditions provided by the first illumination device 217A may be similar to each other. The two latent features may be regularized to approximate a unit Gaussian distribution with mean vectors $(m_{c1}, m_{L1})$. For another set of tube assembly images Sz captured by a second imaging device $C_2$ (e.g., the second imaging device 216B) with lighting condition $L_2$ provided by the second illumination device 217B, latent features related to the camera and lighting conditions are forced to approximate a unit Gaussian distribution with mean vectors $(m_{c2}, m_{L2})$.

By replacing the latent features of a tube image in $S_1$ with vectors $(m_{c2}, m_{L2})$ and reconstructing the image of the tube assembly using the composition model 732, the same tube captured with $C_2$ (the second imaging device 216B) and $L_2$ (second illumination device 217B) will be synthesized. In some embodiments, an adversarial discriminator may be further trained to enforce rules wherein the synthesized image is to be indistinguishable from images in $S_2$ in terms of the camera and the lighting. Similarly, the latent features of a tube assembly image in $S_2$ with $(m_{c1}, m_{L1})$ may be replaced to synthesize images captured with $C_1$ and $L_1$. These processes ensure that image variations are disentangled by the latent space (e.g., latent space 610 and tube interior latent space 618). After training, the trained image decomposition model 730 learns how to perform image decomposition into a disentangled latent space, and the trained image composition model 732 learns how to perform image composition from a latent variable, such as one of the latent variables $L_A$ or $L_B$, in the latent spaces. Since each latent space is disentangled using known variations, a latent vector of a given tube assembly image can be perturbed to generate numerous tube assembly images with desired variations.

In some embodiments, the latent space representation may encode data (e.g., decompose images) across different scales. For example, normalizing flows, autoregressive models, variational autoencoders (VAEs), and deep energy-based models are examples for deep generative learning. Furthermore, the latent space may be constrained to be a known parametric distribution (e.g., Gaussian or mixture-of-Gaussian) or a non-parametric distribution, such as with a vector quantized variational autoencoder (VQ-VAE).

In addition, images other than the generated images can be used as image data to characterize the attributes, such as tube cap classification and tube fluid characterization. The disentangled features in the latent space may also provide useful information (either used as ground-truth annotation or treated as discriminative features) for downstream tasks that may be performed by the system 100. Furthermore, the disentangled features in the latent space can also be used to develop tools that can be used by laboratory personnel, such as vendors, research and development staff, field service technicians, and/or end users (e.g., lab technicians and managers) to evaluate new tube assembly types and tube assembly variations to determine the ability of the system 100 (FIG. 1) to properly characterize the tube assemblies.

In some embodiments, the system 100 may use unpaired image-to-image translation such as cycleGAN to adapt existing data from images of old tube assemblies to images of new tube assemblies. This procedure enables developers of the system 100 and/or tube assemblies to collect field data from the existing tube assemblies when developing new types of tube assemblies.

In some embodiments, image data may be collected in groups that may include dense collections of representative tube assembly types and sparse collections of other similar tube assembly types. Augmented data may be used to fill in missing attributes of images of the sparsely collected tube assembly types. For example, color augmentation may be used to fill in missing colors in the images of sparsely collected tube assembly types.

Figure 8A:
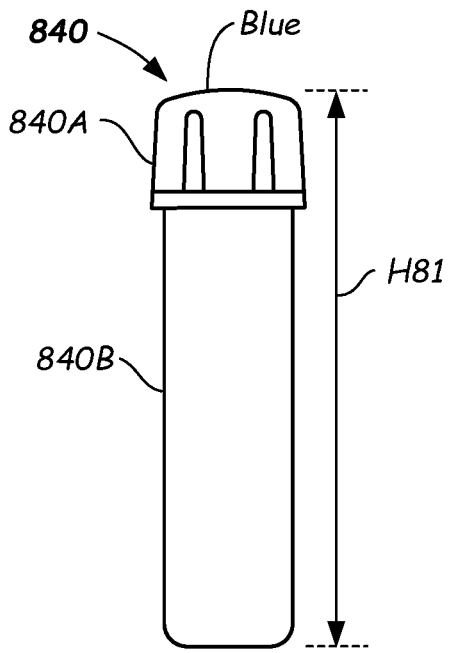
FIGS. 8A and 8B illustrate images of similar tube assemblies, wherein the image of FIG. 8A has a blue cap and the image of FIG. 8B has a green cap.
Figure 8B:
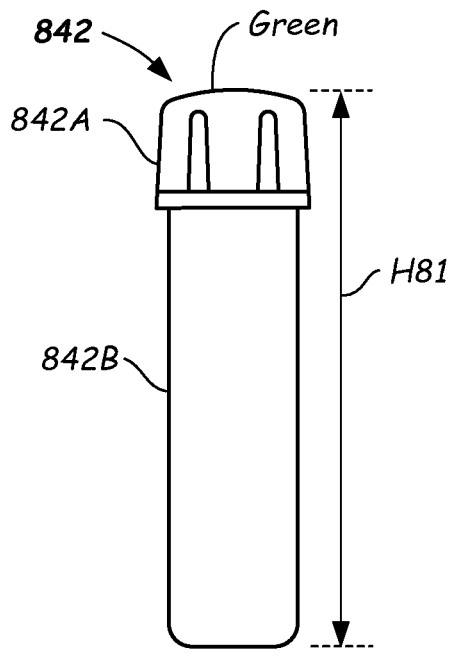

An example of the system 100 synthesizing a tube assembly is described below. Reference is made to FIG. 8A and FIG. 8B, which illustrate images of similar tube assemblies. The tube assembly 840 of FIG. 8A is identical or similar to the tube assembly 842 of FIG. 8B except that the color of the cap 840A of the tube assembly 840 is blue and the color of the cap 842A is green. For example, the tube 840B may be similar to the tube 842B and both the tube assembly 840 and the tube assembly 842 may have the same height H81. The decomposition model 730 may receive an image of the tube assembly 840 as input image A. The decomposition model 730 may also receive an image of the tube assembly 842 as input image B. The decomposition model 730 decomposes the input image A into a set of features (W, X, Y, Z) in the latent space represented as a variable $L_A$ and the image B into a set of features (W', X', Y', Z') in the same latent space represented as a variable $L_B$.

Figure 8C:
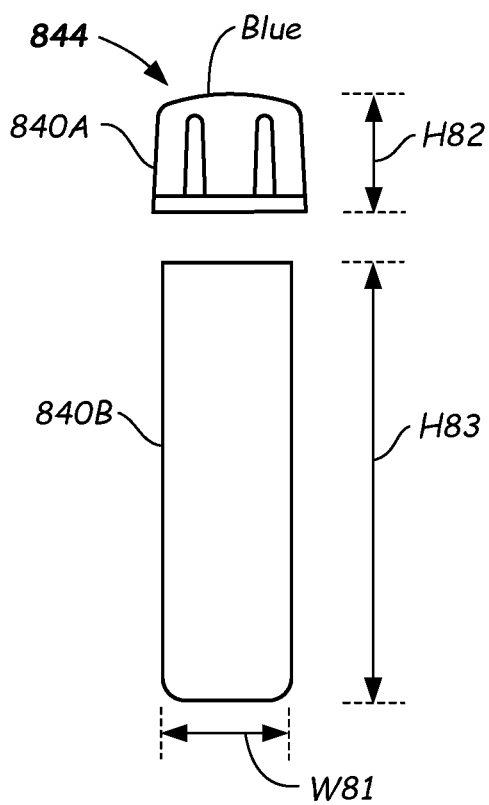
FIG. 8C illustrates an example of a decomposed image of the tube assembly of FIG. 8A according to one or more embodiments.

Additional reference is made to FIG. 8C, which provides an example of a decomposed image 844 of the tube assembly 840. It is noted that other decompositions of the image of the tube assembly 840 may be performed. In the embodiment of FIG. 8C, the feature W may be the cap color, which is blue. The feature X may be the cap height H82, the feature Y may be the tube height H83, and the feature Z may be the tube width W81. Other features may include other portions of the tube geometry or the tube assembly geometry. The composition model 732 may reconstruct the deconstructed image to generate the image A'. The input image A may be compared to the reconstructed image A' by the reconstruction loss module 734. If the loss or difference between the input image A and the reconstructed image A' is within a predetermined amount, the decomposition model 730 and composition model 732 may be considered properly trained and the latent variable $L_A$ is correct for processing the tube assembly 840.

The tube assembly 842 may be selected as a paired image because the only significant difference between the tube assembly 840 and the tube assembly 842 is the color of the caps. The decomposition model 730 may decompose the image B of the tube assembly 842 per the latent space $L_B$. The features of the latent space $L_B$ are the same as with the latent space $L_A$. The feature W' may be the cap color, which is green, the feature X' may be the cap height H82, the feature Y may be the tube height H83, and the feature Z may be the tube width W81. The composition model 732 may compose the deconstructed image to generate the image B'. The input image B may be compared to the reconstructed image B' by the reconstruction loss module 736. If the loss or difference between the input image B and the reconstructed image B' is within a predetermined amount, the decomposition model 730 and composition model 732 may be considered properly trained and the latent variable $L_B$ is correct for processing the tube assembly 842.

The green cap 842A may be a new cap color. In order to reconstruct the tube assembly 842 with a blue cap, the feature W, which is the green cap is substituted with the feature W. The image-to-image reconstruction and other methods may be used to reconstruct the tube assembly 842 with the blue cap. The resulting reconstructed or synthesized image using features W, X', Y', and Z' will be the tube assembly 842A with the blue cap of the tube assembly 840. In some embodiments, the cap 840A as a whole may be used in place of the cap 842A and in other embodiments, the color of the cap 840A may be used in place of the color of the cap 842A. In other embodiments, the color of the cap 840A may be stored and used for the cap 842A without imaging the tube assembly 840.

Figure 9A:
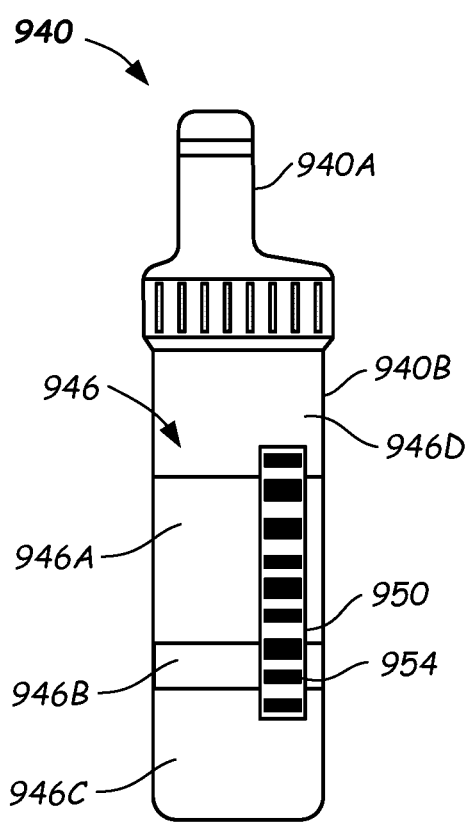
FIGS. 9A-9B illustrate images of tube assemblies having different interior and/or fluid features according to one or more embodiments.
Figure 9B:
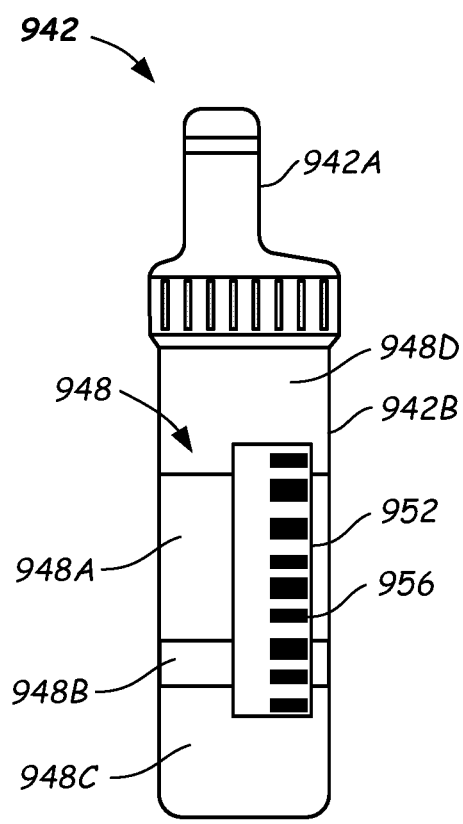

Reference is now made to FIGS. 9A-9B, which illustrate tube assemblies having different interior and/or fluid features that may be used with tube interior latent space 618 (FIG. 6). The tube assembly 940 may include one or more items (e.g., attributes) located in the interior of the tube 940B and may be sealed by a cap 940A. One or more fluids 946 may be located in the interior of the tube 940B and may include a blood serum 946A, a gel separator 946B, and blood 946C. An air gap 946D may be located above the fluids 946.

The tube assembly 942 may include one or more items (e.g., attributes) located in the interior of the tube 942B and may be sealed by a cap 942A. One or more fluids 948 may be located in the interior of the tube 942B and may include blood serum 948A, a gel separator 948B, and blood 948C. An air gap 948D may be located above the fluids 948. The material of the tube 940B and the material of the tube 942B may be similar and may be identified by generating image data through the air gap 946D and the air gap 948D. Accordingly, the attributes of the tube assembly 940 and the tube assembly 942 include, but are not limited to, tube geometry, tube material, tube color, tube surface properties, sample fluid in the tubes, labels affixed to the tube, and lighting condition of the tube during image capture.

All the above attributes of the tube assembly 940 and the tube assembly 942 may be identical or substantially similar. The difference between the tube assembly 940 and the tube assembly 942 may be labels attached to the tube 940B and the tube 942B. The tube assembly 940 has a label 950 affixed to the tube 940B and the tube assembly 942 has a label 952 affixed to the tube 942B. As shown in FIGS. 9A-9B, the label 950 differs from the label 952. For example, the size of the label 950 differs from the size of the label 952 and the position of a barcode 954 differs from the location of a barcode 956.

The decomposition model 730 and the composition model 732 may be configured to identify and/or characterize the attributes of the images of the tube assembly 940 and the tube assembly 942 into features in latent space. Accordingly, the system 100 may be configured to substitute the above features into synthesized images (e.g., image A' or B'). In the example of FIGS. 9A-9B, the system 100 may substitute labels from an original image for either of the label 950 or the label 952 to generate a synthesized image. In some embodiments, the system 100 may substitute labels, but keep the original bar code or other label information in the synthesized image.

In some embodiments, the synthesized tube assembly images are used by the system 100 during a tube assembly identification process. For example, when tube assemblies 102 are loaded into the input/output instrument 104A, images of the tube assemblies 102 may be captured by the imaging device 116 or another imaging device. Images of synthesized tube assemblies may be used for tube assembly identification of tube assemblies that were not initially recognized by the tube characterization model 126C. The tube assemblies may then be characterized and transported to the appropriate instruments 102 where the samples are analyzed as described herein. In some embodiments, the instruments 102 may perform processes, such as aspiration, that are customized to the identified tube assemblies. In other embodiments, the robot 108 (FIG. 1) may move sample containers to and from carriers 114 using specific techniques, such as specific grasping techniques, depending on the type of identified tube assemblies.

Figure 10:
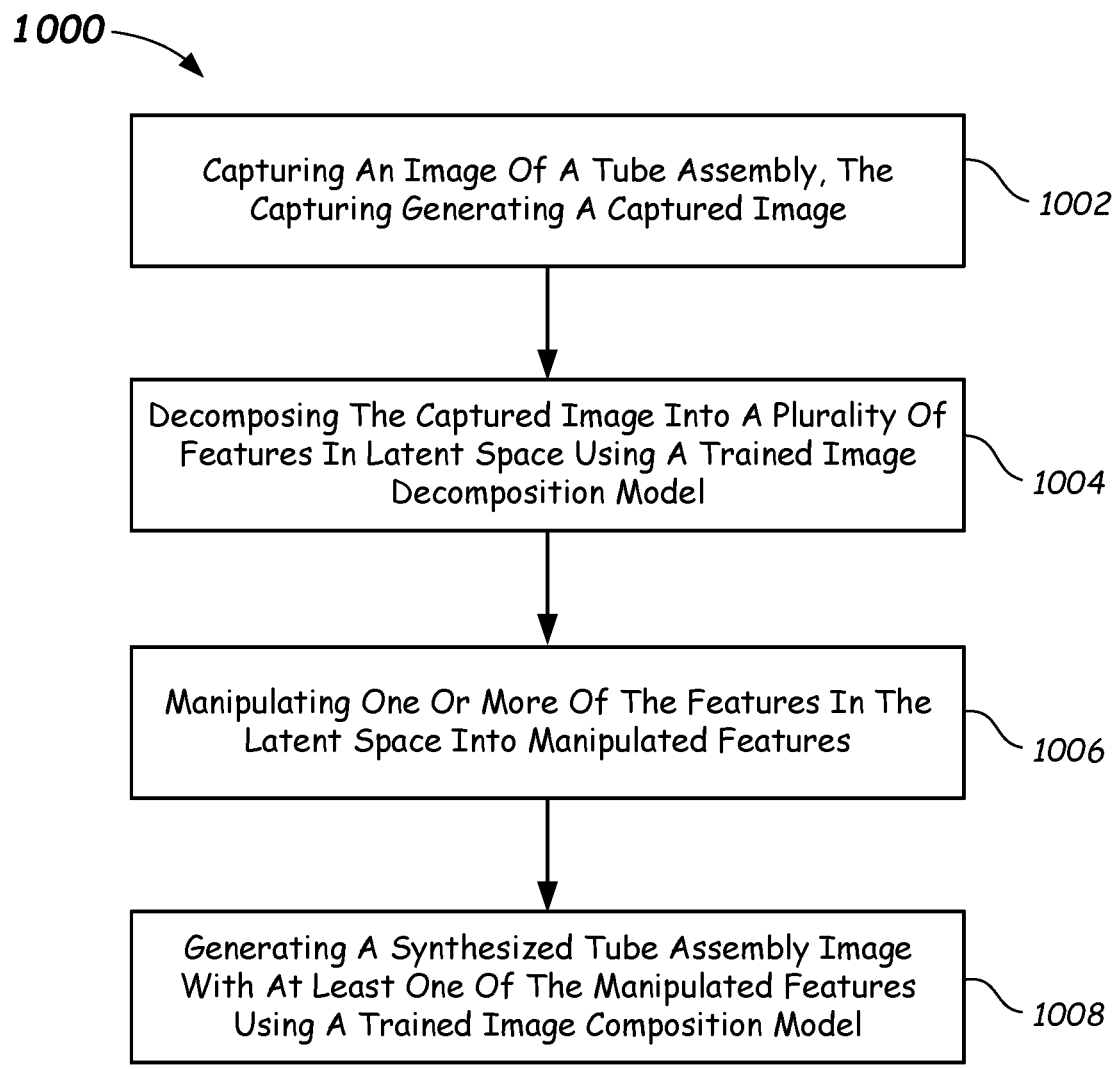
FIG. 10 is a flowchart illustrating a method of synthesizing an image of a tube assembly according to one or more embodiments.

Reference is now made to FIG. 10, which is a flowchart illustrating a method 1000 of synthesizing an image of a tube assembly (e.g., tube assembly 202). The method 1000 includes, at 1002, capturing an image of a tube assembly, the capturing generating a captured image. The method 1000 includes, at 1004, decomposing the captured image into a plurality of features (e.g., features 612) in latent space (e.g., latent space 610) using a trained image decomposition model (e.g., image decomposition model 502). The method 1000 includes, at 1006, manipulating one or more of the features in the latent space into manipulated features. For example, a cap color may be changed from red to blue and/or a cap shape may be changed from round to oval. Other features may be additionally or alternatively changed (i.e., manipulated). The method 1000 includes, at 1008, generating a synthesized tube assembly image with at least one of the manipulated features using the trained image composition model (e.g., image composition model 504).

Figure 11:
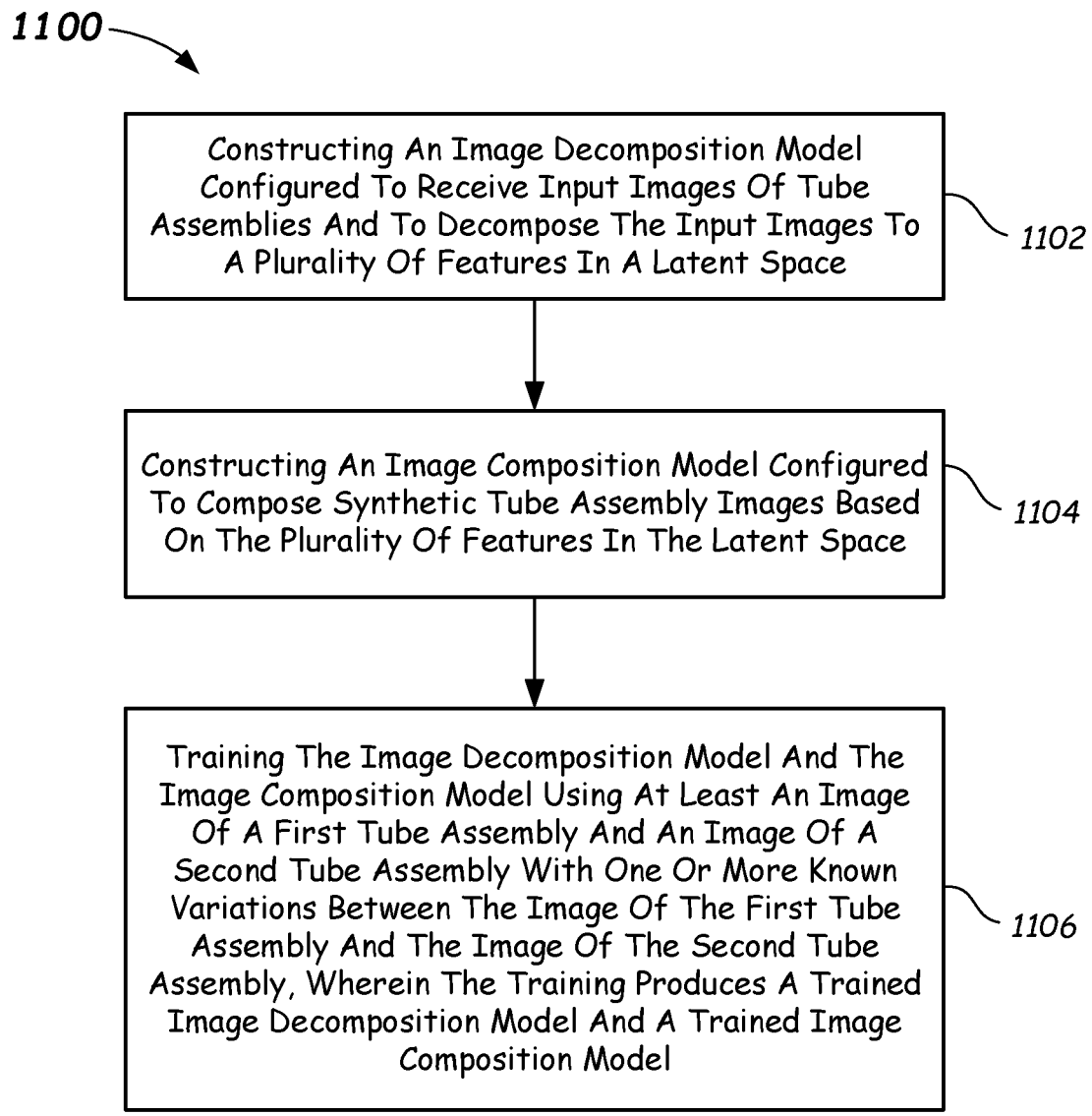
FIG. 11 is a flowchart illustrating another method of synthesizing an image of a tube assembly according to one or more embodiments.

Reference is now made to FIG. 11, which is a flowchart illustrating a method 1100 of synthesizing images of tube assemblies (e.g., tube assembly 202). The method 1100 includes, at 1102, constructing an image decomposition model (e.g., image decomposition model 502) configured to receive input images of tube assemblies and to decompose the input images into a plurality of features (e.g., features 612) in a latent space (e.g., latent space 610). The method 1100 includes, at 1104, constructing an image composition model (e.g., image composition model 504) configured to compose synthetic tube assembly images based on the plurality of features in the latent space. The method 1100 includes, at 1106, training the image decomposition model and the image composition model using at least an image of a first tube assembly (e.g., tube assembly 840) and an image of a second tube assembly (e.g., tube assembly 842) with one or more known variations between the image of the first tube assembly and the image of the second tube assembly, wherein the training produces a trained image decomposition model and a trained image composition model.

While the disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure but, to the contrary, to cover all modifications, equivalents, and alternatives falling within the scope of the claims.

What is claimed is:

1. A method of synthesizing an image of a tube assembly, comprising:
   capturing an image of a tube assembly, the capturing generating a captured image;
   decomposing the captured image into a plurality of features in latent space using a trained image decomposition model;
   manipulating one or more of the features in the latent space into manipulated features; and
   generating a synthesized tube assembly image with at least one of the manipulated features using a trained image composition model.

2. The method of claim 1, further comprising training an image decomposition model and an image composition model using at least an image of a first tube assembly and an image of a second tube assembly, wherein there are one or more known variations between the image of the first tube assembly and the image of the second tube assembly, the training producing the trained mage image decomposition model and the trained image composition model.

3. The method of claim 2, wherein the training the decomposition model is at least partially based on a reconstruction loss between synthesized images and input images.

4. The method of claim 1, wherein the tube assembly comprises a tube and a cap and at least one of the plurality of features is tube geometry, tube color, tube surface property, cap geometry, cap color, or lighting condition.

5. The method of claim 1, wherein the tube assembly comprises a tube and at least one of the plurality of features is tube geometry, tube material, sample fluid in the tube, label affixed to the tube, or lighting condition of the tube.

6. A method of synthesizing images of tube assemblies, comprising:
   constructing an image decomposition model configured to receive input images of tube assemblies and to decompose the input images into a plurality of features in a latent space;
   constructing an image composition model configured to compose synthetic tube assembly images based on the plurality of features in the latent space; and
   training the image decomposition model and the image composition model using at least an image of a first tube assembly and an image of a second tube assembly with one or more known variations between the image of the first tube assembly and the image of the second tube assembly, wherein the training produces a trained image decomposition model and a trained image composition model.

7. The method of claim 6, further comprising:
   capturing an image of a tube assembly, the capturing generating a captured image;
   decomposing the captured image into a plurality of decomposed features in the latent space using the trained image decomposition model;
   manipulating one or more of the decomposed features in the latent space into manipulated features; and
   generating a synthesized tube assembly image with at least one of the manipulated features using the trained image composition model.

8. The method of claim 6, wherein the training the decomposition model is at least partially based on a reconstruction loss between synthesized images and input images.

9. The method of claim 6, wherein the image composition model is trained based on a reconstruction loss between synthesized images and input images.

10. The method of claim 6, wherein at least one of the features in the latent space is generated using computer-generated imagery.

11. The method of claim 6, wherein images of at least two of the tube assemblies differ from each other with one or more controlled attributes.

12. The method of claim 6, wherein images of at least two tube assemblies share one or more attributes in common.

13. The method of claim 6, wherein at least one of the image decomposition model or the image composition model is trained based on a reconstruction loss without the images of the tube assemblies.

14. The method of claim 6, wherein the tube assemblies comprise a tube and a cap and at least one of the plurality of features in the latent space is tube geometry, tube color, tube surface property, cap color, cap geometry, or lighting condition.

15. The method of claim 6, wherein the tube assemblies comprise a tube and at least one of the plurality of features in the latent space is tube geometry, tube material, sample fluid in the tube, label affixed to the tube, or lighting condition of the tube.

16. The method of claim 6, wherein one or more features in the latent space include a fluid property in a tube assembly.

17. A diagnostic laboratory system, comprising:
an image decomposition model configured to receive input images of tube assemblies and to decompose the input images into a plurality of features in a latent space; and
an image composition model configured to compose synthetic tube assembly images based on the plurality of features in the latent space,
wherein the image decomposition model and the image composition model are trained using at least an image of a first tube assembly and an image of a second tube assembly with one or more known variations between the image of the first tube assembly and the image of the second tube assembly.

18. The diagnostic laboratory system of claim 17, wherein the image decomposition model is trained at least partially based on a reconstruction loss between synthesized images and input images.

19. The diagnostic laboratory system of claim 17, wherein the image composition model is trained based on a reconstruction loss between synthesized images and input images.

20. The diagnostic laboratory system of claim 17, wherein the tube assemblies comprise a tube and a cap and at least one of the plurality of features in the latent space is tube geometry, tube color, tube surface property, cap color, cap geometry, or lighting condition.

* * * * *